(12) United States Patent
Phillips et al.

(10) Patent No.: US 8,818,482 B2
(45) Date of Patent: Aug. 26, 2014

(54) ELECTRODE PATCH MONITORING DEVICE

(76) Inventors: Paul David Phillips, County Down (GB); Brian McGregor, County Down (GB); Wesley James McKean, Londonderry (GB)

( * ) Notice: Subject to any disclaimer, the term of this patent is extended or adjusted under 35 U.S.C. 154(b) by 325 days.

(21) Appl. No.: 12/992,851

(22) PCT Filed: May 15, 2009

(86) PCT No.: PCT/US2009/003043
§ 371 (c)(1),
(2), (4) Date: Mar. 7, 2011

(87) PCT Pub. No.: WO2009/139911
PCT Pub. Date: Nov. 19, 2009

(65) Prior Publication Data
US 2011/0190615 A1  Aug. 4, 2011

Related U.S. Application Data

(60) Provisional application No. 61/054,008, filed on May 16, 2008.

(51) Int. Cl.
*A61B 5/0408* (2006.01)
*H01R 43/00* (2006.01)

(52) U.S. Cl.
USPC .......... 600/393; 600/372; 600/391; 600/392; 29/825

(58) Field of Classification Search
CPC ............. A61B 5/04085; A61B 2562/046; A61B 2562/0209; A61B 2562/164
USPC .................... 600/393, 372, 391, 392
See application file for complete search history.

(56) References Cited

U.S. PATENT DOCUMENTS

| | | | | |
|---|---|---|---|---|
| 4,461,304 A * | 7/1984 | Kuperstein | .............. | 600/378 |
| 4,763,660 A * | 8/1988 | Kroll et al. | .............. | 600/391 |
| 4,852,572 A * | 8/1989 | Nakahashi et al. | ......... | 600/391 |
| 5,327,888 A * | 7/1994 | Imran | .............. | 600/393 |
| 6,055,448 A * | 4/2000 | Anderson et al. | ......... | 600/372 |
| 6,584,343 B1 * | 6/2003 | Ransbury et al. | ......... | 600/509 |
| 7,941,202 B2 * | 5/2011 | Hetke et al. | .............. | 600/377 |

* cited by examiner

*Primary Examiner* — Lee S Cohen
(74) *Attorney, Agent, or Firm* — Foster Pepper PLLC; Richard A. Koske; P. G. Scott Born

(57) ABSTRACT

An electrode patch monitoring device that enables fast and accurate application is described. According to some embodiments, the electrode patch monitoring device comprises an array of electrodes for monitoring bioelectrical data that are formed on a flexible substrate. The electrode patch monitoring device may be available in a plurality of sizes, and various methods are provided for selecting an appropriate size according to the physiology of a patient. Methods for applying the electrode patch monitoring device to the patient's body are also provided.

11 Claims, 9 Drawing Sheets

ELECTRODE PATCH MONITORING DEVICE

BACKGROUND

1. Field of Disclosure

The present disclosure relates generally to an electrode patch monitoring device comprising an array of electrodes for monitoring bioelectric data, and to a methods for selecting an appropriately sized device and applying the device to a patient.

2. Discussion of Related Art

An electrocardiograph (ECG) is a device comprising a plurality of electrodes applied to the skin of a patient in the thoracic region. Depending on their positions on the patient's body, these electrodes measure electrical activities in different areas of the cardiac muscle from different directions. An ECG is a useful tool for diagnosing various cardiac disorders and, in the case of acute myocardial infarction (also known as heart attack), for identifying damage to the cardiac muscle.

A traditional 12-lead ECG comprises a number of electrodes, usually ten, placed at specific points on the patient's body, primarily on the front of the chest. Here a "lead" refers to a notional line formed by a plurality of electrodes, wherein electrical signals are measured along the notional line. While a 12-lead ECG provides an important first-line assessment of abnormalities of the cardiac muscle, it has been known to miss ST elevation myocardial infarction (STEMI) occurring at the back surface of the heart. More recent ECG devices utilize many more electrodes, e.g., 40 to 100 electrodes, placed both on the front and on the back of the patient, in order to provide more comprehensive information on the electrical activity of a patient's heart.

For example, U.S. Pat. No. 6,055,448 describes a sensor device suitable for use with an ECG system. The sensor device comprises an anterior portion and a posterior portion, to be attached respectively to the front and back of the thorax of a patient. The anterior portion comprises an assembly of 64 electrodes and 4 limb leads, which are formed on a flexible substrate that comprises a plurality of finger-like portions. The finger-like substrate portions are applied, using an adhesive, to the front thoracic region. The lateral spacing between adjacent finger-like substrate portions is adjustable to enable proper electrode placement with respect to a variety of chest sizes. A plurality of electrodes are formed on each finger-like substrate portion. Conductive traces associated with the electrodes may be connected to an apparatus that delivers signals to and/or receives signals from the electrodes. Although the sensor device can be applied to a wide range of body sizes, the application may be cumbersome. In particular, in the case of a small body size, excess substrate material may detract from comfort and may catch onto other objects, potentially pulling some electrodes away the patient's skin and/or disturbing the electrical signals.

SUMMARY

Various embodiments relate to an electrode patch monitoring device that enables fast and accurate application. According to some embodiments, the electrode patch monitoring device comprises an array of electrodes for monitoring bioelectrical data, the electrodes being formed on a flexible substrate. The electrode patch monitoring device may be available in a plurality of sizes, and various methods are provided for selecting an appropriate size according to the physiology of a patient. Methods for applying the electrode patch monitoring device to the patient's body are also provided.

One embodiment is directed to a sensor device for monitoring bioelectrical data. The sensor device comprises first and second electrically conductive traces formed on a flexible substrate, an electrically insulating layer overlaid on at least a portion of the first electrically conductive trace and at least a portion of the second electrically conductive trace, and a first electrode for receiving a bioelectric signal. The first electrode is formed at least in part on a portion of the electrically insulating layer directly over the second electrically conductive trace, and is electrically connected with the first electrically conductive trace and electrically insulated from the second electrically conductive trace.

Another embodiment is directed to a method for forming on a flexible substrate a plurality of electrodes in a predefined pattern. The method comprises forming on the flexible substrate a plurality of electrically conductive traces, forming an electrically insulating layer over the plurality of electrically conductive traces, the electrically insulating layer comprising a plurality of apertures to expose ends of each of the plurality of electrically conductive traces, and forming a plurality of electrodes on the flexible substrate. Each of the plurality of electrodes forms an electrical connection with an end of at least one of the plurality of electrically conductive traces, and at least one of the plurality of electrodes is formed at least in part on the electrically insulating layer.

A further embodiment is directed to a method for applying to a patient a sensor device for monitoring bioelectric data. The method comprises selecting a sensor device of an appropriate size at least in part by measuring a predetermined anatomical distance or by comparing said predetermined anatomical distance against at least one predetermined length, removing a portion of a backing material from a flexible substrate of the sensor device to expose at least some adhesive, positioning the sensor device on the patient's body in a predetermined orientation and applying the at least some adhesive onto the patient's skin. At least one indicium on the flexible substrate is aligned with a prescribed anatomical region of the patient's body. Orientation of the sensor device with respect to the patient's body is maintained. Alignment between the at least one indicium and the prescribed anatomical region of the patient's body is also maintained.

DETAILED DESCRIPTION

Compared with a traditional 12-lead ECG, the sensor device of U.S. Pat. No. 6,055,448 provides more data on the electrical activities of the cardiac muscle. Furthermore, the formation of electrodes on a substrate of the sensor device allows a plurality of electrodes to be applied as a group, rather than individually. However, application of the sensor device is still relatively time-consuming, because the finger-like substrate portions need to be aligned individually. Other difficulties may also arise in applying the sensor device to a patient. For example, while a first finger-like substrate portion is being applied by a clinician, other finger-like substrate portions may bend and pull in undesired directions, making it difficult for the clinician to properly align and attach the first finger-like substrate portion. In addition, two finger-like substrate portions may become attached to each other by accident.

The Applicant has recognized that it would be desirable to reduce the amount of time and effort required to apply an assembly of electrodes onto a patient's body. Accordingly, the Applicant has developed an electrode patch monitoring device that can be applied to a patient quickly and easily.

1. General Description

Figure 1:
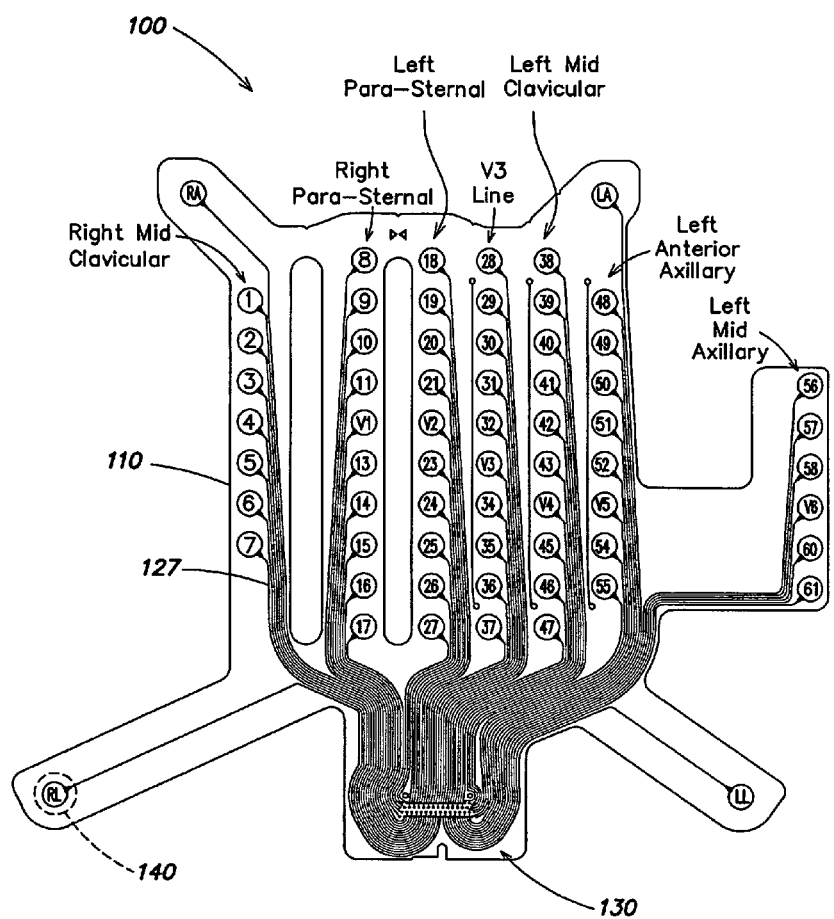
FIG. 1 is a plan view of an anterior portion of an electrode patch monitoring device according one embodiment.
Figure 2:
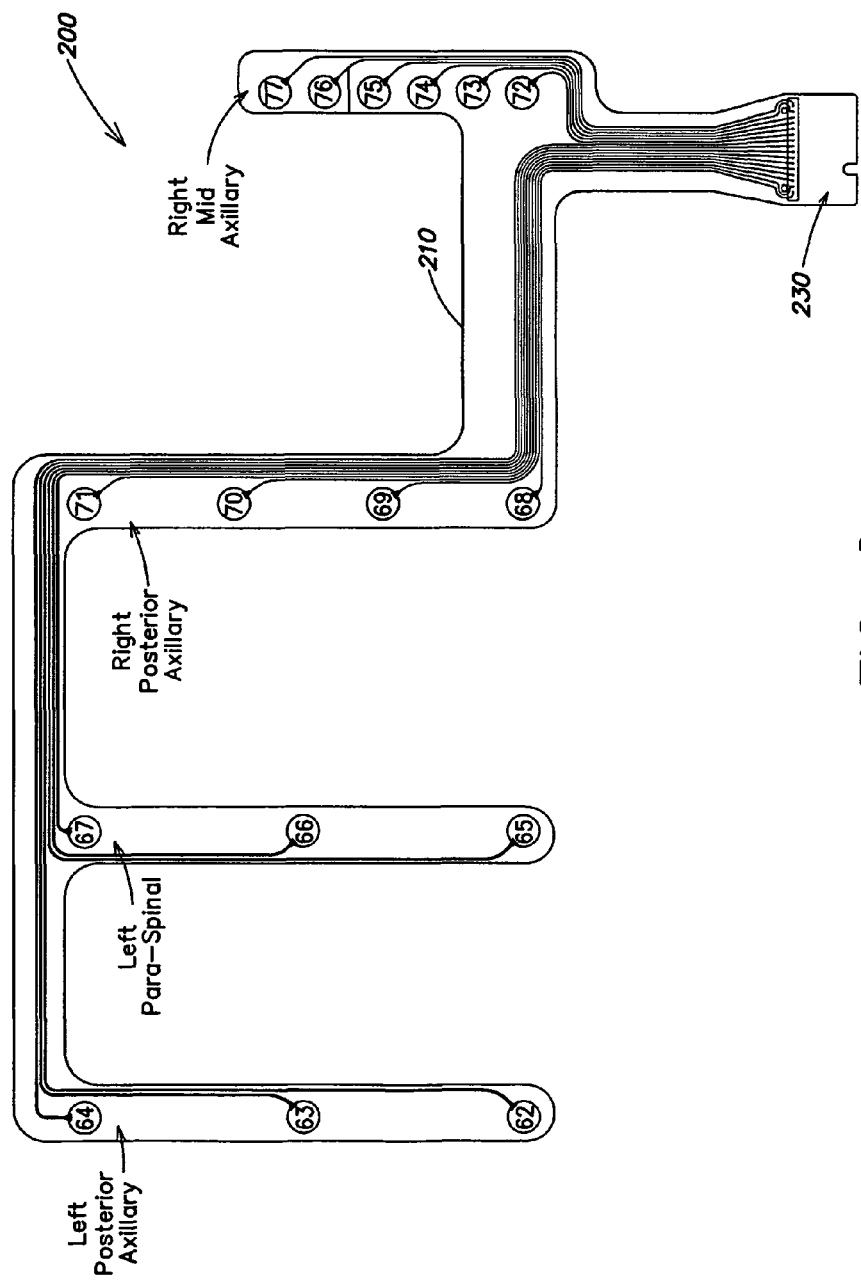
FIG. 2 is a plan view of a posterior portion of an electrode patch monitoring device according to another embodiment.

According to some embodiments, an electrode patch monitoring device comprises an anterior portion and a posterior portion, to be attached respectively to the front and back of the thorax of a patient. FIG. 1 shows an example of an anterior portion 100, and FIG. 2 shows an example of a posterior portion 200. Note that the view shown in FIG. 1 is the so-called doctor side, that is, it is as seen by a doctor when the anterior portion is applied to a patient. According to the embodiment shown in FIG. 1, the electrodes are formed behind the substrate, so that the electrodes may come into contact with the patient's skin. In other words, the electrodes are formed on the side of the substrate facing the patient's skin, which is also referred to as the skin side. The view shown in FIG. 2 is also the doctor side.

The anterior portion 100 shown in FIG. 1 comprises 65 electrodes formed on a flexible substrate 110. The electrodes are labeled 1-11, 13-21, 23-32, 34-43, 45-52, 54-58, 60-61, V1-V6, RA, LA, RL, and LL, respectively. The locations of electrodes V1-V6, RA, LA, RL, and LL coincide with those traditionally used in a 12-lead ECG, with RA (right arm), LA (left arm), RL (right leg), and LL (left leg) being the limb leads and V1-V6 running across the thorax.

As shown in FIG. 1, each electrode is electrically connected with at least one conductive trace, which runs from the electrode to a cable clamp area 130 near the bottom of the anterior portion 100. For example, electrode 7 is connected with trace 127, which ends in the cable camp area 130. A cable clamp is a device that can be mounted at area 130 to connect the electrodes to a signal processing device, so that bioelectrical signals received from the electrodes are relayed to the signal processing device. A cable clamp may comprise various leads to form electrical connections with the conductive traces. Examples of such cable clamp are disclosed in U.S. Pat. No. 5,733,151, which is hereby incorporated by reference herein. It should be appreciated that the anterior portion may be used in conjunction with any suitable devices that collect and process the bioelectrical signals received from the electrodes. One example of a suitable apparatus is the interface unit 11 and the storage, processing, and display unit 12 disclosed in U.S. Pat. No. 6,721,593. Further examples are disclosed in U.S. Pat. No. 5,419,337. Both patents are hereby incorporated by reference herein. However, the use of these devices is not required, as many suitable devices are possible.

Each conductive trace may end at a predetermined location within the cable clamp area 130. Alignment of conductive traces within area 130 ensures proper connections with leads in the cable clamp for transmission of bioelectrical signals from the electrodes to the signal processing device. Of course, the cable clamp area 130 may be located elsewhere on the substrate 110, or omitted entirely. Electrical connection means other than cable clamp area 130 may optionally be employed.

The conductive traces may be arranged into several groups, each group comprising parallel traces serving the same column of electrodes. Each such group of traces may be placed between adjacent columns of electrodes, allowing some of the traces to reach electrodes located near the top of the electrode patch. For example, traces associated with electrodes 18-21, V2, and 23-27 are placed between the column comprising electrodes 18-21, V2, and 23-27 and the column comprising electrodes 28-32, V3, and 34-37.

Referring to FIG. 2, the posterior portion 200 comprises substrate 210, electrodes 62-77, cable clamp area 230, and a plurality of conductive traces. As with the anterior portion 100 of FIG. 1, each electrode of the posterior portion 200 is electrically connected with at least one conductive trace, which may be further connected to a signal processing device via a cable clamp mounted at area 230.

The posterior portion 200 shown in FIG. 2 is merely one example of a posterior electrode array that may optionally be used in conjunction with anterior portion 100. Other exemplary posterior electrode arrays that may be used are described in U.S. Pat. No. 6,055,448, which is hereby incorporated herein by reference. Further, while the posterior portion provides additional bioelectric data, e.g., data from the back of a patient's heart, the posterior portion need not be used.

It should also be appreciated that the surface appearances, sizes, and shapes of electrodes and conductive traces shown in the illustrative embodiments are merely exemplary. Other surface appearances, sizes, and shapes may be used depending on any number of factors, such as production cost, signal sensitivity, and/or aesthetic appeal. Similarly, the described quantities and arrangements of electrodes and conductive traces on the substrate are merely exemplary, and may be selected to enable the desired measurement of bioelectric signals from a patient. For example, according to other embodiments, the number of electrodes for the anterior portion (or both the anterior portion and posterior portion) may be any number greater than 12, any number greater than 60, any number between and including 40 and 100, any number between and including 50 and 70, or approximately 60.

2. Substrate Sheet

Figure 3:
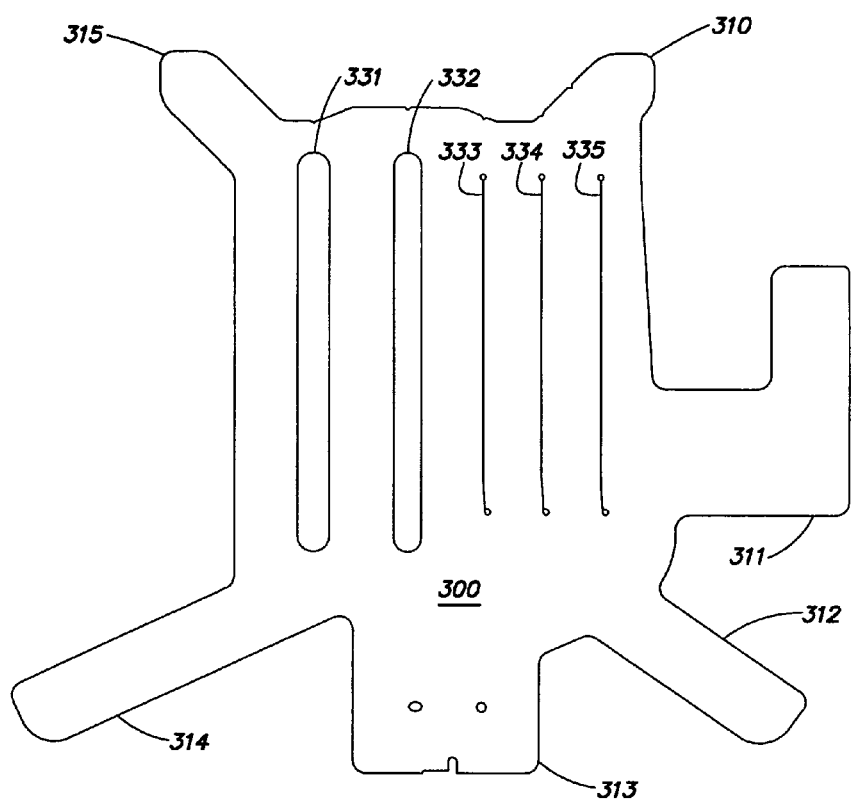
FIG. 3 shows the shape of the substrate according to a further embodiment.

According to some embodiments, electrodes for monitoring bioelectric data are formed on a single sheet of flexible substrate. Although excess portions of substrate material may be removed or omitted during production, structural integrity of the substrate is preserved substantially. That is, the substrate remains substantially sheet-like, which allows the entire assembly of electrodes to be aligned and applied in substantially one motion. For example, the substrate in FIG. 3 is without fingers or slats, such that the external perimeter or periphery of the substrate does not encroach on the central electrode area.

In addition to providing fast and accurate application of electrodes, a substantially unitary structure can improve the repeatability of measurements, because it reduces the likelihood that certain substrate portions are applied in slightly different positions on the same patient during different monitoring sessions, which may result in significantly different positioning of an electrode relative to other electrodes. The substantially unitary structure can also improve predictability of measurements across different patients.

According to one embodiment, the anterior portion of an electrode patch monitoring device comprises a flexible substrate sheet made of a dielectric material. This material may be transparent, translucent, or opaque. One example of a suitable dielectric material is Autostat CT3, which is a heat stabilized polyester film manufactured by MacDermid Inc. Initially, the substrate sheet may be a rectangle having dimensions of at least 3 ft (0.91 m) by 2 ft (0.61 m). During production, excess substrate material may be cut and removed, resulting in a cut-out shape such as the one shown in FIG. 3. Other methods, such as molding, may also be used to form the substrate.

The center portion 300 of the substrate closely resembles a rectangle. Extending from the center portion 300 are six protrusions 310-315 of various lengths. Four of the protrusions, 310, 312, 314, and 315, extend radially outward from the corners of the center portion 300. These protrusions support the limb leads, such as electrodes RA, RL, LA, and LA shown in FIG. 1. A fifth protrusion 311 extends to the right of the center portion 300, and supports a column of electrodes to be attached to the side of the patient's body, for example, electrodes 56-58, V6, and 60-61 shown in FIG. 1. A sixth protrusion 313 extends downward from the center portion 300, providing a location at which a cable clamp can be mounted to connect the electrode patch monitoring device to a signal processing device.

Vertical slots 331-335 of various widths may be cut and removed from the interior of the center portion 300, or otherwise formed as part of the substrate. Slots 331-335 allow the substrate to curve simultaneously in multiple dimensions, for example, to conform to the contour of a female chest. Moreover, when the electrode patch is applied to a patient's skin, slots 331-335 provide ventilation to the skin to reduce buildup of moisture due to, for example, perspiration. For reasons that will become clear, excess moisture on the patient's skin may prevent proper functioning of the electrode patch monitoring device.

It should be appreciated that the widths of slots 331-335 are not limited to those depicted in FIG. 3. For example, the width of slot 331 may vary depending on the lateral spacing between the column comprising electrodes 1-7 and the column comprising electrodes 8-11, V1, 13-17, as shown in FIG. 1. This lateral spacing may in turn depend on the sizing of the electrode patch monitoring device, which will be further described below. It is also possible that a slot has negligible width; for example, slot 335 may simply be a vertical slit in the substrate sheet.

3. Sizing of Electrode Patch Monitoring Device

According to some embodiments, each electrode patch monitoring device has a fixed size, which ensures proper positioning of electrodes when applied to a patient whose chest size falls within a certain range. This enables fast and accurate application of the entire electrode assembly. A plurality of sizes are provided to accommodate different physiologies, and such sizes differ primarily in the distance between adjacent columns of electrodes. For practical reasons, it may be desirable to have a relatively small number of different sizes (e.g., three, four, or five), while providing that any common chest size can be mapped to at least one size for the electrode patch monitoring device.

An anatomical dimension that may be used in determining the appropriate spacing between adjacent columns of electrodes is the distance between the inner edges of a patient's shoulder joints. The Applicant has recognized that, compared to total chest size, this distance is less variable across the population. As a result, a relatively small number of sizes, e.g., three or four different sizes, may be sufficient to accommodate a complete range of chest sizes. After selecting an electrode patch monitoring device of an appropriate size for a particular patient, a clinician is able to smooth the flexible substrate onto the patient's body, without having to adjust the lateral spacing between adjacent columns of electrodes. This eliminates the need to bend or to fold excess substrate material that extends laterally, connecting columns of electrodes.

Figure 4:
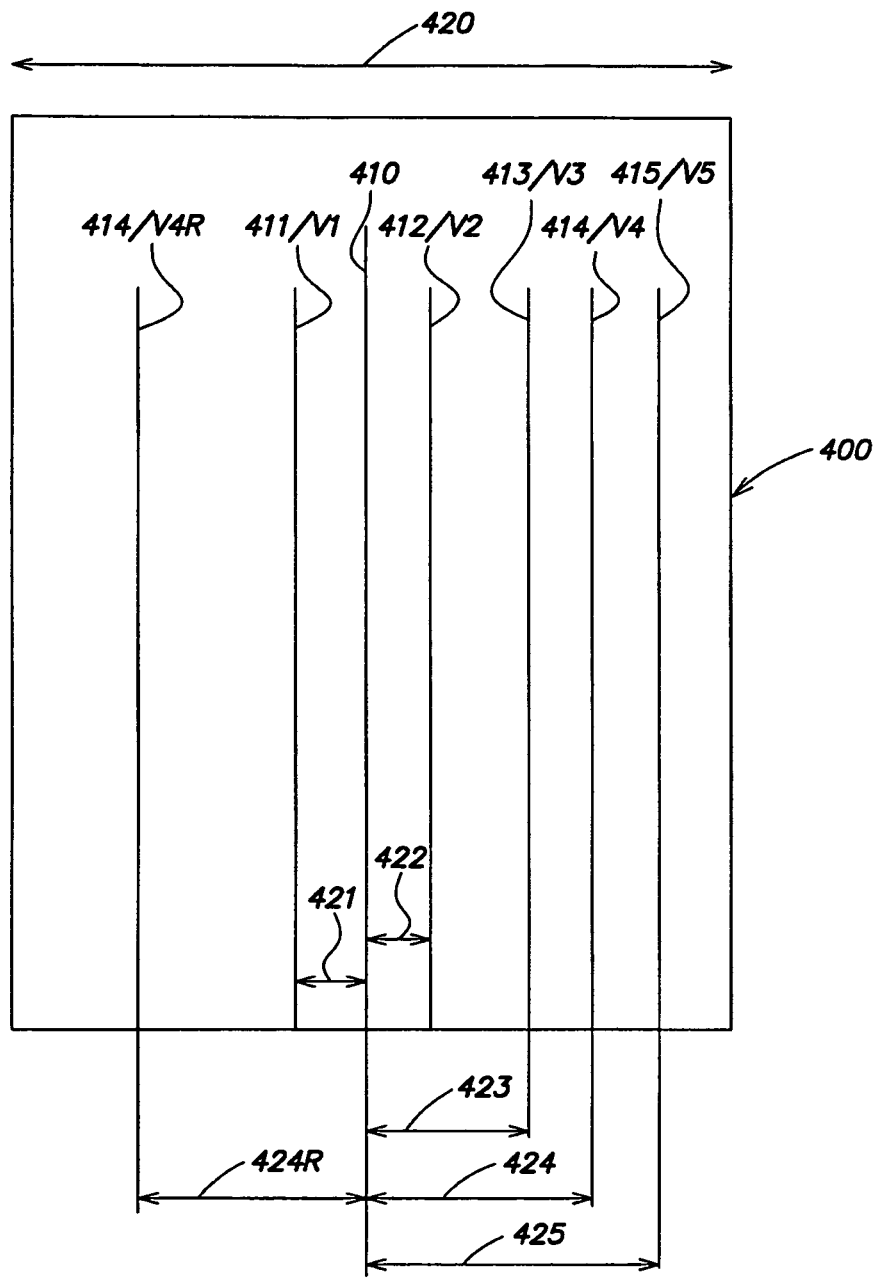
FIG. 4 illustrates key dimensions in positioning electrode columns on an anterior portion of an electrode patch monitoring device according to some embodiments.

FIG. 4 illustrates some anatomical dimensions used in determining the sizing of an electrode patch monitoring device according to one embodiment. Distance 420 is the distance between the inner edges of the patient's shoulder joints, which in this embodiment is also the distance between the electrodes RA and LA, as shown in FIG. 1. Line 410 corresponds to the center line of a patient's chest. Lines 411-415 and 414R indicate the center lines of the electrode columns. Thus, distances 421-425 and 424R are the respective distances between the electrode columns and the center line 410. Note that lines 411-415 and 414R also correspond to the longitudinal locations of electrodes in a traditional 12-lead ECG. For example, electrode V1 in a 12-lead ECG is located along line 411 and electrode V2 is located along line 412.

According to some embodiments, distances 421-425 and 424R are increased for larger sizes. Table 1, below, provides exemplary values for distances 421-425 and 424R for a set of sizes labeled "Small," "Medium," "Large," and "Extra Large." All distances are in centimeters. Of course, both the use of a set of four sizes and the particular dimensions for those sizes are merely exemplary. The values provided may also be approximate.

TABLE 1

| Distance Label(s) | Small | Medium | Large | XLarge |
|---|---|---|---|---|
| 420 | 25 | 30 | 35 | 40 |
| 421, 422 | 2 | 2.5 | 3 | 3.5 |
| 423 | 5.5 | 6.75 | 8 | 9.25 |
| 424, 24R | 9 | 11 | 13 | 15 |
| 425 | 12.5 | 15 | 17.5 | 20 |

4. Forming Electrodes and Conductive Traces

Electrodes and conductive traces may be formed on a substrate by a number of well known methods, such as flexographic printing with conductive inks or chemical etching of metals. In some embodiments, both the electrodes and conductive traces are screen printed onto the substrate using silver-doped conductive ink, such as Silver Electrodag PF 410, manufactured by Nor-Cote® International, Inc. Both electrodes and conductive traces may be formed on the substrate on the skin side (i.e., the side facing the patient's skin). Alternatively, electrodes and conductive traces may be formed on the doctor side (i.e., the side facing a doctor as the monitoring device is applied onto a patient), and openings may be formed on the substrate sheet to allow electrical connections between the patient's skin and the electrodes and between the electrodes and the conductive traces.

According to some embodiments, a layer of non-conductive ink is printed over the conductive traces once the conductive ink is dried under a heat or UV curing process. An example of a suitable non-conductive ink is SD 2460 Flex ink, also manufactured by Nor-Cote®. This insulating layer may prevent moisture from accumulating between two parallel conductive traces and effectively shorting the two traces. A likely source of moisture is perspiration from the patient's skin.

It is desirable that an insulating layer, if used, does not cover the ends of conductive traces in the cable clamp area 130 shown in FIG. 1, so that proper electrical connections may be formed between the conductive traces and the leads in a cable clamp. Also, it is desirable that the insulating layer does not entirely obscure the electrodes on the skin side of the electrode patch monitoring device, as doing so may inhibit or prevent the reception of electrical signals from the patient's body. According to some embodiments, the electrodes may be covered by an adhesive that is electrically conductive. An example of such adhesive material is PR00034 63B Hydrogel, which is manufactured by Covidien™. Such material may be heat or UV cured into gel pads covering the electrodes. The gel pads may secure the electrodes on the patient's skin at prescribed locations, while providing a conductive pathway between the electrodes and the patient's skin. An exemplary gel pad, located on the skin side of the electrode patch monitoring device, is shown as gel pad 140 in FIG. 1.

The surface appearances, sizes, shapes and arrangements of the insulating layer and adhesive gel pads described herein are merely exemplary. Other surface appearances, sizes, shapes, and arrangements may be used depending on any number of factors, such as production cost, signal sensitivity, and/or aesthetic appeal.

The widths of conductive traces may be determined by a combination of factors, such as conductivity, impedance, cost of conductive ink, and/or precision of printing. For example, screen printed traces that are too narrow may not provide reliable connectivity due to inherent limitations in the screen printing process. Furthermore, traces may have variable widths so that impedance remains the same for traces of different lengths. For traces that are screen printed using silver-doped ink, a width between 0.5 millimeters and 2 millimeters may offer a good balance between impedance and reliability.

The spacing between adjacent traces may also depend on a combination of factors. For example, in the case of screen printing, placing traces very close to each other may result in conductive ink seeping from one trace to another and effectively shorting the two traces. Moreover, since a group of parallel traces may be placed between two adjacent columns of electrodes, the amount of available lateral space for the group of traces may be limited by the distance between the two adjacent electrode columns. This limit may be especially severe in the case of a smaller sized electrode patch monitoring devices, which include electrode columns placed close to each other to accommodate smaller chest sizes. In consideration of the foregoing limitations, the Applicant has developed a novel production technique called "bridging," which is described in greater detail below.

5. Bridging Technique

The Applicant has recognized that, in a smaller sized electrode patch monitoring device, there may be insufficient lateral spacing between adjacent columns of electrodes to accommodate the necessary number of conductive traces that are printed parallel to each other. For example, according to the embodiment described in FIG. 4 and Table 1, distance 422 for the "Small" size is 2 cm and distance 423 for the same size is 5.5 cm. Subtracting distance 422 from distance 423, the distance between lines 412 and 413 is 3.5 cm. Assuming the diameter of each electrode is roughly 2 cm, this leaves roughly 1.5 cm between the electrode column centered at line 412 and the electrode column centered at line 413. Clearly, this is insufficient for a group of 10 traces (e.g., traces associated with the electrodes centered along line 412), assuming each trace has a width of 1 millimeter and each pair of adjacent traces have a space of 1 millimeter between them.

Figure 5:
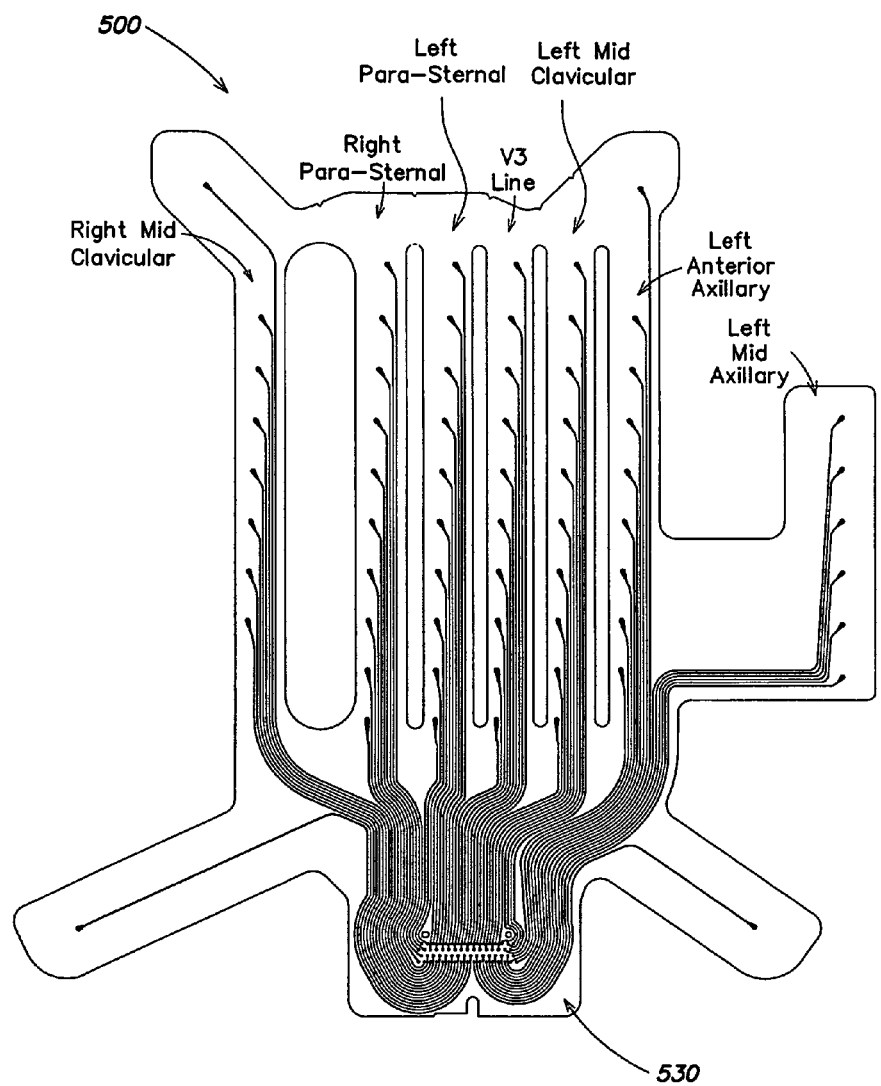
FIG. 5 shows a first step of forming an electrode patch monitoring device according to some embodiments, the step comprising printing conductive traces on the substrate.

To overcome this difficulty, electrodes may be formed over conductive traces, while ensuring that each electrode is electrically insulated from conductive traces serving other electrodes. It should be appreciated that an electrode should generally be electrically isolated from a conductive trace connected to another electrode. Otherwise, the two electrodes become electrically shorted and unable to provide the desired measurements of bioelectrical activities. To prevent undesirable electrical connections between electrodes and conductive traces, a layer of electrically insulating material is formed between the electrodes and the conductive traces. According to some embodiments, a production method for an electrode patch monitoring device comprises three production phases. During the first production phase, conductive traces are formed on the substrate in a predetermined pattern. This is shown in FIG. 5. Each trace starts from a first predetermined location in the cable clamp area 530 and extends upward, ending in a second predetermined location. The second predetermined location is chosen such that a connection between the trace and its associated electrode will be made when the associated electrode is formed during a subsequent production phase.

Figure 6:
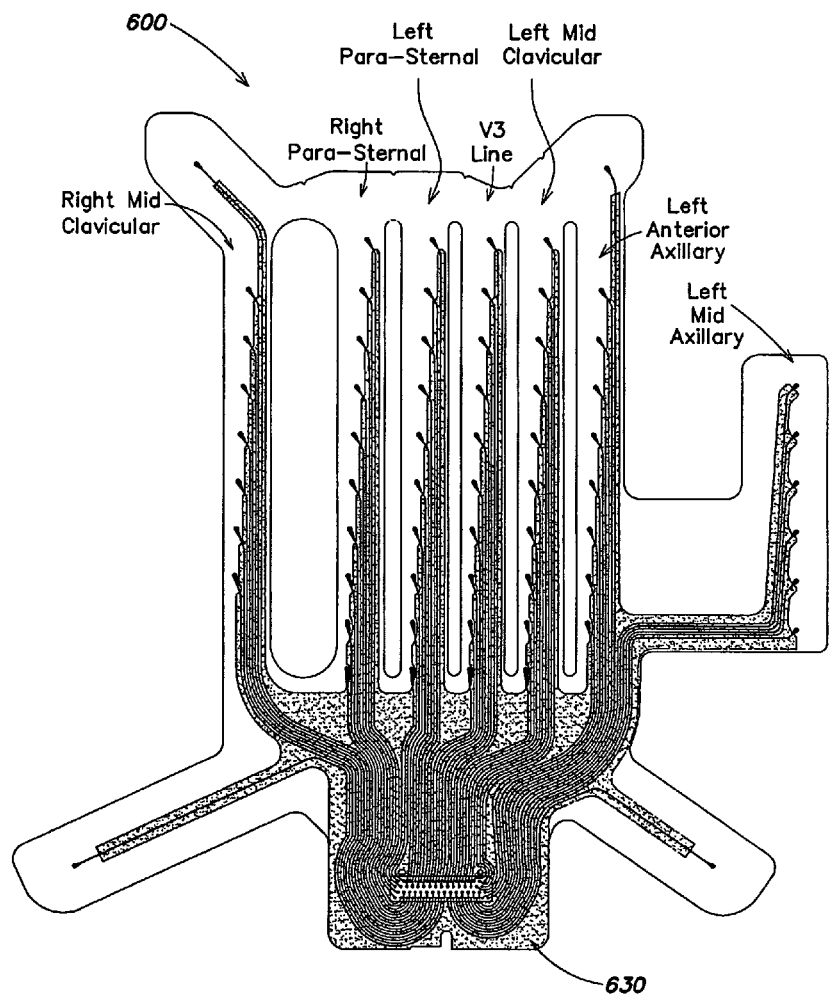
FIG. 6 shows a second step of forming an electrode patch monitoring device according to some embodiments, the step comprising printing a layer of insulating material over parts of the conductive traces.

During the second production phase, a layer of insulating material is formed over the conductive traces, leaving both ends of each trace exposed. This is shown in FIG. 6.

Figure 7:
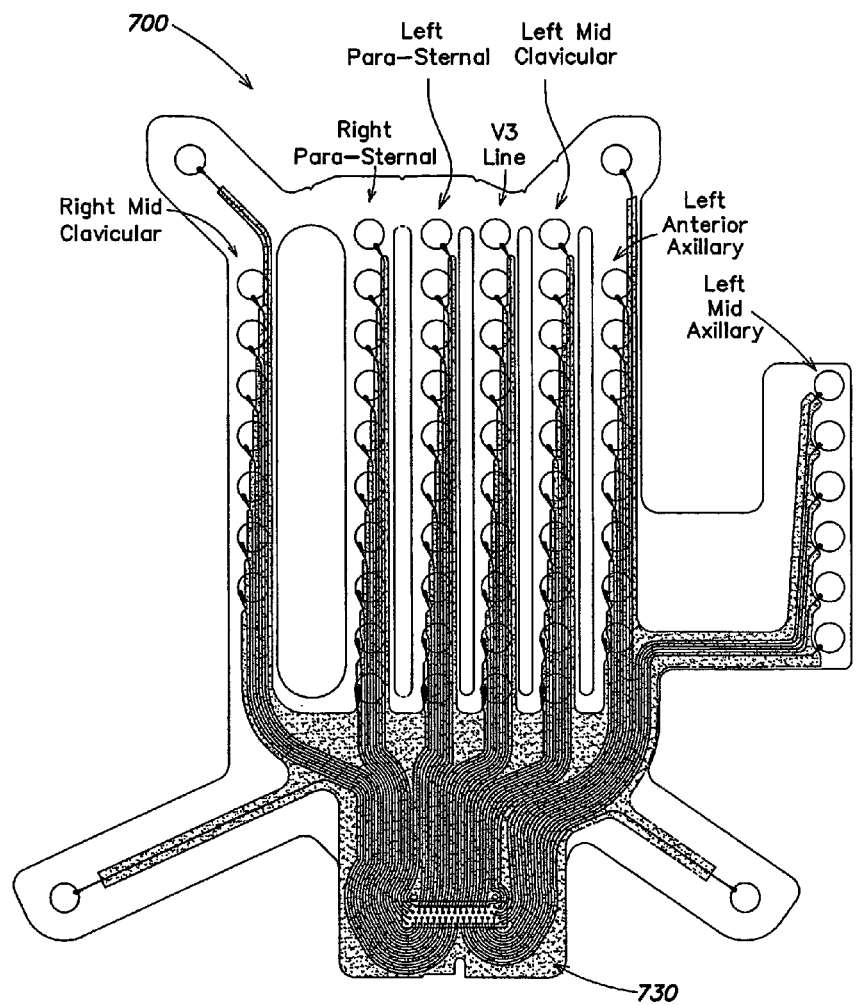
FIG. 7 shows a third step of forming an electrode patch monitoring device according to some embodiments, the step comprising forming electrodes on the substrate, at least partially over the insulating layer.

During the third production phase, columns of electrodes are formed on the substrate. This is shown in FIG. 7. As described above, the location of the upper end of each conductive trace is chosen such that the conductive trace becomes electrically connected with its associated electrode when the associated electrode is formed. Furthermore, there is at least one electrode that is formed over one or more conductive traces associated respectively with one or more other electrodes. In other words, the electrode "bridges" over one or more conductive traces (or vice versa).

Figure 8:
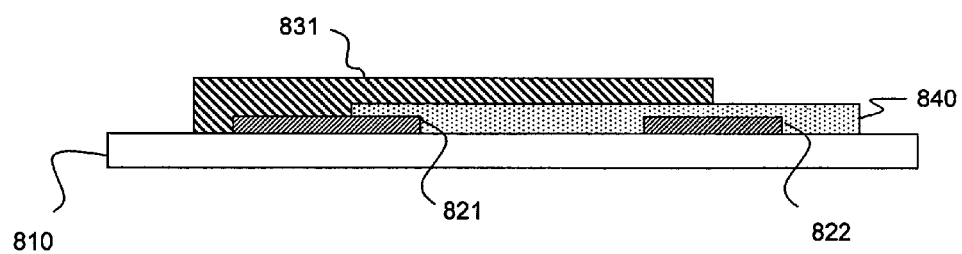
FIG. 8 is a side view illustrating the bridging of an electrode over a conductive trace.

FIG. 8 is a side view illustrating the bridging of an electrode 831 over a conductive trace 822. At the particular location shown in FIG. 8, insulating layer 840 leaves a portion of conductive trace 821 exposed, so that electrode 831 and trace 821 are in direct contact and form an electrical connection. By contrast, electrode 831 is entirely insulated from conductive trace 822 by insulating layer 840, even though a portion of electrode 831 is formed above a portion of conductive trace 822. This prevents undesirable electrical connection between electrode 831 and conductive trace 822, which lies underneath electrode 831.

It should be appreciated that the above described bridging technique may advantageously be applied in a similar manner to other sizes of electrode patch monitoring devices described herein. Thus, the technique is not limited to smaller sizes.

6. Methods for Applying an Electrode Patch Monitoring Device

The Applicant has recognized that the finger-like projections of the sensor device of U.S. Pat. No. 6,055,448 may require an undesirable amount of time and effort to apply. Each of the finger-like projections needs to be aligned individually with an appropriate anatomic region, which can be a lengthy and laborious process. There is a need for a monitoring device that facilitates fast application, so that patient data can be made available quickly, and clinicians can devote their time to other tasks.

Individual alignment of the finger-like substrate portions also increases the likelihood that each portion is applied at slightly different positions during different monitoring sessions. This may result in substantially different positioning of a particular electrode relative to other electrodes. There is also a need for a monitoring device that facilitates repeatability of measurements.

Furthermore, U.S. Pat. No. 6,055,448 discloses that the finger-like substrate portions may be joined at the base by laterally extending substrate portions, on which conductive traces are formed in order to connect electrodes with a signal receiving apparatus. When the sensor device is used on a small patient, the finger-like substrate portions are placed close to each other, and the excess substrate in the lateral substrate portions need to be bent or folded. This may lead to a number of problems. For example, the excess substrate, and the conductive traces thereupon, may flex due to air currents or movements of the patient, causing noise in the electrical signals. The same flexing may also cause nearby electrodes to lose contact with the patient's skin. Therefore, it is desirable to reduce the excess in lateral substrate portions.

The electrode patch monitoring device described herein can be applied in substantially one motion, with little or no excess substrate when applied to a patient, which may alleviate some of the problems described above. According to some embodiments, the electrode patch monitoring device comprises a flexible substrate that is substantially rectangular in shape, with various protrusions to support limb leads, additional electrodes, and a cable clamp that connects the electrode patch monitoring device to a signal processing device. Due to its substantially unitary construction, application of an electrode patch monitoring device may be accomplished quickly and easily. As an illustrative example, a method for applying an electrode patch monitoring device is described below.

First a clinician selects an electrode patch of an appropriate size for a particular patient. The size is selected based on the distance between the inner edges of the patient's shoulder joints. According to one embodiment, the clinician may obtain a numeric measurement of this distance and compare the measurement with ranges provided (e.g., in user guidelines) for the electrode patch monitoring device. For example, user guidelines may state that a "Small" electrode patch should be used for patients having a distance between shoulder joints that is between 20 cm and 27 cm.

According to another embodiment, a line or other indication of distance may be printed on the packaging material of the electrode patch monitoring device. The clinician may hold the packaging material up to the patient's chest to determine whether the line or indication substantially corresponds with the distance between the inner edges of the patient's shoulder joints. If so, the electrode patch monitoring device contained within the packaging material is deemed to be an appropriate size for the patient. FIGS. 9(a)-9(d) illustrate packages 900a-d for a set of four electrode patch monitoring devices of different sizes: a small size, a medium size, a large size, and an extra large size, respectively. Each has a corresponding line or indication 910a-d representing a predetermined distance that may be compared to the distance between the inner edges of the patient's shoulder joints, or some other anatomical distance, in a manner described herein.

Figure 9:
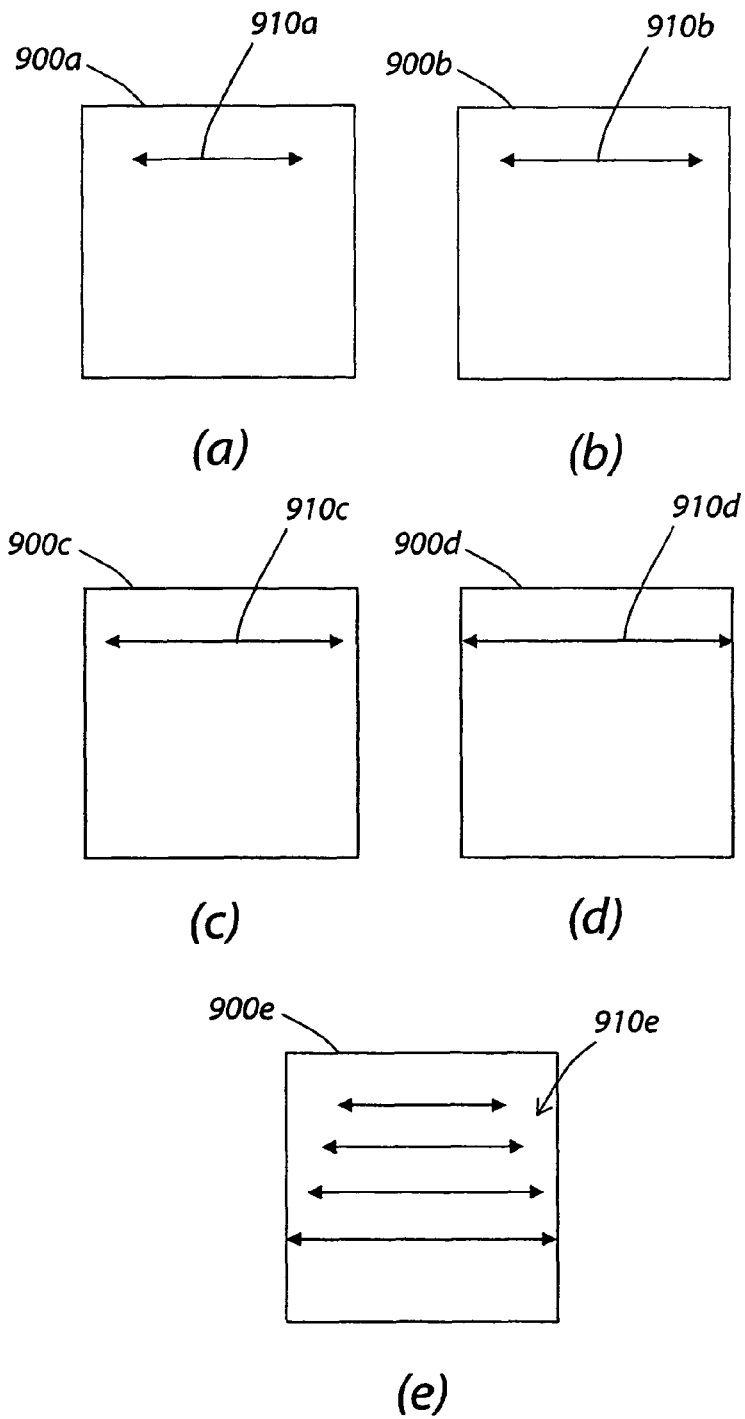
FIGS. 9(a)-9(e) illustrate exemplary packaging materials for the electrode patch monitoring devices.

Alternatively, a plurality of such lines or indicia may be provided, each corresponding to a different size, and the clinician may hold the packaging material (or another material) up to the patient's chest to determine the best correspondence between the plurality of lines or indicia and the distance between the inner edges of the shoulder joints (or some other suitable anatomical distance). An example package 900e having a plurality of such lines or indicia 910e is shown in FIG. 9(e). The best correspondence may be, for example, the closest approximation, the closest over-approximation, or the closest under-approximation. The selected line or indicia may then dictate the size of electrode patch monitoring device to be used for this particular patient. Of course, the size selection can be done in a number of other ways, for example, based on clothing size or another anatomical dimension, such as shoulder size generally.

Next, the clinician removes a portion of backing material from the flexible substrate of the electrode patch monitoring device. In doing so, some, but not all, of the adhesive gel pads attached to the electrodes are exposed. For example, the clinician may peel off a portion of backing material from the top of the electrode patch monitoring device, where positioning indicia may be printed, thereby exposing gel pads attached to the electrodes in the top row. Leaving many gel pads unexposed decreases the likelihood that a gel pad will become accidentally attached to the patient at an undesirable location during the alignment process.

The clinician proceeds to position the electrode patch monitoring device onto the patient's chest, for example, by aligning indicia printed on the substrate with prescribed anatomical locations. For instance, there may be two arrows printed near the top center of the substrate, respectively labeled "RIGHT PARA-STERNAL" and "LEFT PARA-STERNAL," as shown in FIG. 1. The two arrows point to a common point, which may be aligned with the patient's sternal notch. The clinician may align at least two separate indicia with two distinct anatomical locations, thereby ensuring that the orientation of the electrode patch monitoring device is correct.

Having obtained proper positioning and orientation, the clinician secures the electrode patch in place by applying the exposed adhesive onto the patient's skin. There should generally be sufficient exposed adhesive to ensure that the electrode patch does not shift thereafter.

Once it is ascertained that the electrode patch is properly positioned, the clinician removes remaining backing material and smoothes the electrode patch onto the patient's body. Since an appropriate size has been selected for this particular patient, there is no need to adjust the positions of individual electrode columns. In other words, once the initial positioning is completed, all remaining electrodes are self-aligning. As a result, there is no or little excess substrate extending laterally between the electrode columns. As described above, this may reduce signal noise by reducing the flexing of conductive traces in air currents.

Considering the flexible nature of the substrate, the clinician may choose not to remove the remaining back material all at once. Instead, the clinician may remove the backing material one small portion at a time and apply the exposed adhesive gel pads before removing another portion of backing material. Again, this may prevent a gel pad from becoming accidentally attached to the patient at an undesirable location while the clinician is applying gel pads at other locations.

After use, the electrode patch may be removed from the patient's skin by peeling off the adhesive gel pads. To facilitate removal, the substrate may be removed in portions corresponding to the strips separating the slots. For example, notches provided along the top edge of the substrate, as shown in FIG. 3, map be used to facilitate tearing the substrate in the region above the slots so that the strips may be peeled away individually.

Having thus described several aspects of at least one embodiment, it is to be appreciated that the present disclosure is not limited to the details of construction and the arrangement of components set forth in the foregoing description or illustrated in the drawings. Various alterations, modifications, and improvements may readily occur to those skilled in the art. Such alterations, modifications, and improvements are intended to be within the spirit and scope of the present disclosure. Accordingly, the foregoing description and drawings are by way of example only.

Further, although certain advantages of the devices and methods described herein have been expressed, these advantages are provided merely to illustrate potential applications, etc., of such devices and methods, and do not define necessary or required features. The phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A sensor device for monitoring bioelectrical data, the sensor device comprising:
   first and second electrically conductive traces formed on a flexible substrate;
   an electrically insulating layer overlaid on at least a portion of the first electrically conductive trace and at least a portion of the second electrically conductive trace; and
   a plurality of electrodes for receiving bioelectric signals, each of the plurality of electrodes being formed at least in part on one or more portions of the electrically insulating layer directly over the second electrically conductive trace;
   wherein at least one electrode of the plurality of electrodes is in direct contact and electrically connected with the first electrically conductive trace and is electrically insulated from the second electrically conductive trace.

2. The sensor device of claim 1, wherein the electrically insulating layer comprises an aperture, and wherein the first electrically conductive trace forms an electrical connection with the at least one electrode via the aperture.

3. The sensor device of claim 1, further comprising:
   a first electrode for receiving a bioelectric signal, the first electrode being formed on the flexible substrate and being electrically connected with the second electrically conductive trace.

4. The sensor device of claim 3, further comprising:
   a third electrically conductive trace formed on the flexible substrate, wherein the at least one electrode is formed at least in part on a second portion of the electrically insulating layer directly over the third electrically conductive trace and the at least one electrode is electrically insulated from the third electrically conductive trace.

5. The sensor device of claim 1, wherein the flexible substrate comprises first and second parallel slots, and wherein the first slot extends along a first side of the at least one electrode and the second slot extends along a second, opposite side of the at least one electrode.

6. The sensor device of claim 5, wherein at least a portion of each of the first and second electrically conductive traces extend lengthwise in a direction parallel to the first and second slots.

7. The sensor device of claim 5, wherein the sensor device comprises a first column of the plurality of electrodes between the first and second parallel slots.

8. The sensor device of claim 7, wherein a plurality of electrodes in the first column of electrodes are formed at least in part on one or more portions of the electrically insulating layer directly over the second electrically conductive trace.

9. The sensor device of claim 1, wherein the flexible substrate comprises a plurality of parallel slots separated by a plurality of a plurality of strips, and wherein each strip of the plurality of strips comprises a column of the plurality of electrodes formed thereon.

10. The sensor device of claim 9, wherein each of the plurality of parallel slots extends more than half of the length of the substrate.

11. The sensor device of claim 9, wherein a respective distance between each pair of adjacent columns of the plurality of electrodes is fixed.

\* \* \* \* \*